United States Patent [19]

Dahl

[11] 4,140,132
[45] Feb. 20, 1979

[54] VARIABLE RATE TIMER FOR A CARDIAC PACEMAKER

[76] Inventor: Joseph D. Dahl, 815 E. 51 St., Minneapolis, Minn. 55417

[21] Appl. No.: 889,219

[22] Filed: Mar. 23, 1978

[51] Int. Cl.² ................................................ A61N 1/36
[52] U.S. Cl. ........................... 128/419 PG; 128/419 B
[58] Field of Search .......... 128/419 B, 419 P, 419 PG, 128/419 PT

[56] References Cited

U.S. PATENT DOCUMENTS

| | | | |
|---|---|---|---|
| 3,456,134 | 7/1969 | Ko ..................................... | 128/419 B |
| 3,563,245 | 2/1971 | McLean et al. ................. | 128/419 PS |
| 3,593,718 | 7/1971 | Krasner et al. ................ | 128/419 PG |
| 3,777,762 | 12/1973 | Nielsen ........................... | 128/419 PG |
| 3,830,242 | 8/1971 | Greatbatch ..................... | 128/419 PT |
| 3,835,864 | 9/1974 | Rasor et al. ..................... | 128/419 B |
| 4,009,721 | 3/1977 | Alcidi ............................. | 128/419 PG |

OTHER PUBLICATIONS

Myers et al., "IEEE Transactions on Biomedical Engineering, vol. 10, No. 2, Apr. 1963, p. 83.

Primary Examiner—William E. Kamm
Attorney, Agent, or Firm—Leo Gregory

[57] ABSTRACT

A timing device having a self-generating voltage source to modify the constant rate of a cardiac pacemaker in which the resulting improvement consists in making the constant rate of a cardiac pacemaker a variable rate as a function of physical activity.

12 Claims, 3 Drawing Figures

VARIABLE RATE TIMER FOR A CARDIAC PACEMAKER

BACKGROUND OF THE INVENTION

1. Field of the Invention

This invention relates to varying the pacing pulse rate of cardiac pacemakers.

2. Description of the Prior Art

Prior art cardiac pacemakers in general provide a substantially fixed or constant rate pacing pulse and such a pacing pulse does not vary with or accommodate the demands of varying physical activity.

SUMMARY OF THE INVENTION

The invention herein provides for the modification or conversion of a prior art type of cardiac pacemaker having a fixed or constant rate pulsing pace to adapt the same to provide a variable pacing pulse having a rate which is a function of physical activity.

It is an object of the invention herein therefore to provide a relatively simple and highly reliable device to vary the rate of the pacing electronic pulse of a cardiac pacemaker to make the rate a function of physical activity.

It is more generally an object of the invention herein to provide a heart beat control rate which increases or decreases in rate as a function of physical activity and which decreases in rate in a manner analagous to the general reduction in rate of a natural heart beat after having been subjected to physical activity.

More specifically it is an object of the invention herein to provide a device which embodies a cantilever suspended element which constitutes a high impedance voltage generator such as a piezo-electric element, which when subjected to motion vibrates to provide alternating voltage from the resulting strain upon it, said alternating voltage then being diode rectified, stores in a capacitive network wherein it is proportional to physical activity, and is applied to an appropriate field effect transistor having its drain source path acting as a variable resistance to provide in a cardiac pacemaker a pacing or timing pulse rate which varies as a rate of physical activity.

It is also an object of this invention to provide a high impedance self-generating voltage source which is a function of motion and which provides variable timing for an otherwise constant or fixed pacing pulse rate of a cardiac pacemaker, the rate of which will vary as a function of physical activity of the subject wearing the pacemaker.

These and other objects and advantages of the invention will be set forth in the following description made in connection with the accompanying drawings in which like reference characters refer to similar parts throughout the several views.

DESCRIPTION OF A PREFERRED EMBODIMENT

Figure 1:
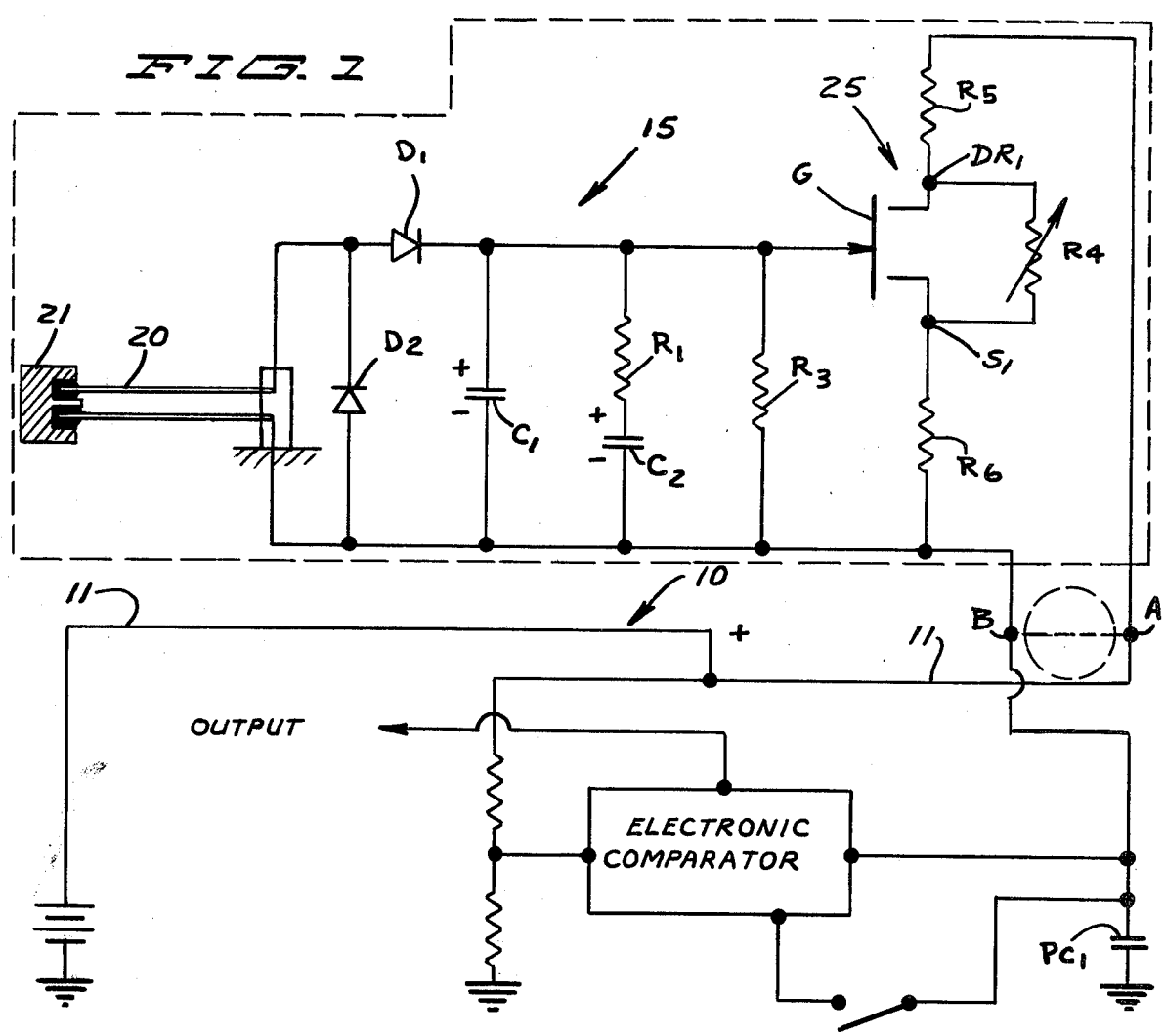
FIG. 1 is a schematic wiring diagram showing the invention herein.

The invention herein is shown as a device in connection with a prior art cardiac pacemaker and comprises means to provide said pacemaker with a variable heart beat control rate herein called a pacing pulse rate and is indicated generally by the reference numeral 15 and is shown in a preferred embodiment as a schematic diagram in FIG. 1.

The device as here described is shown mounted on a substrate or chip 17 and may be suitably encapsulated in an insulated mount in a known manner as indicated at 19 and has outwardly extending terminals A and B for attachment to the circuitry of a cardiac pacemaker.

Figure 2:
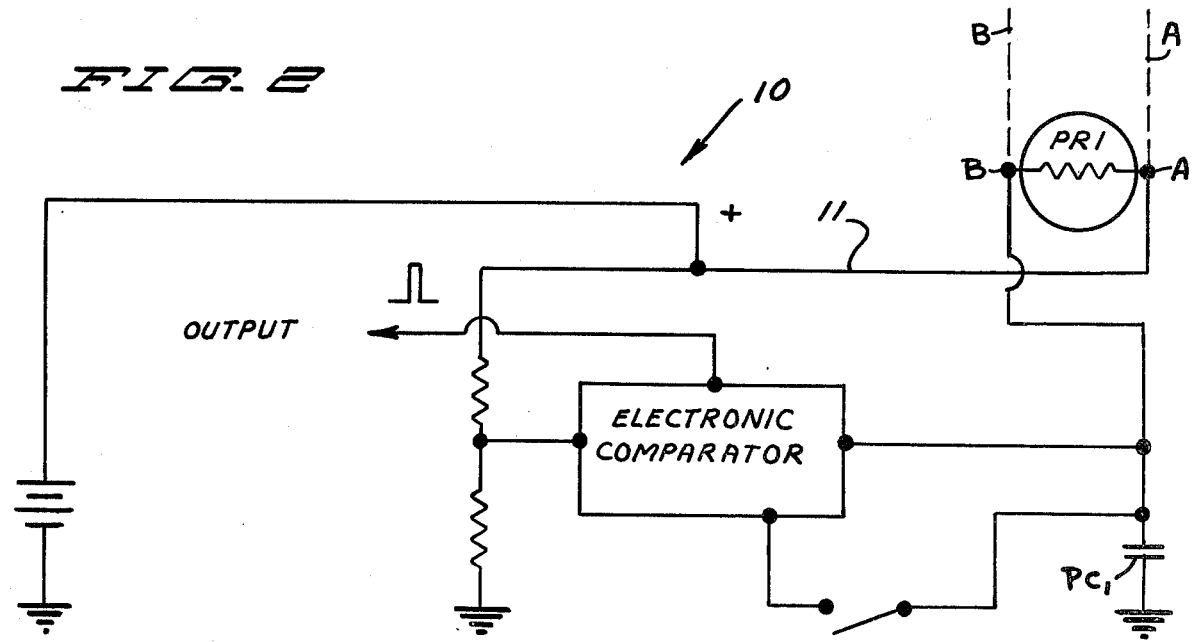
FIG. 2 is a schematic wiring diagram showing a prior art constant rate pacemaker circuit in which there is indicated the portion for which the invention herein is substituted.
Figure 3:
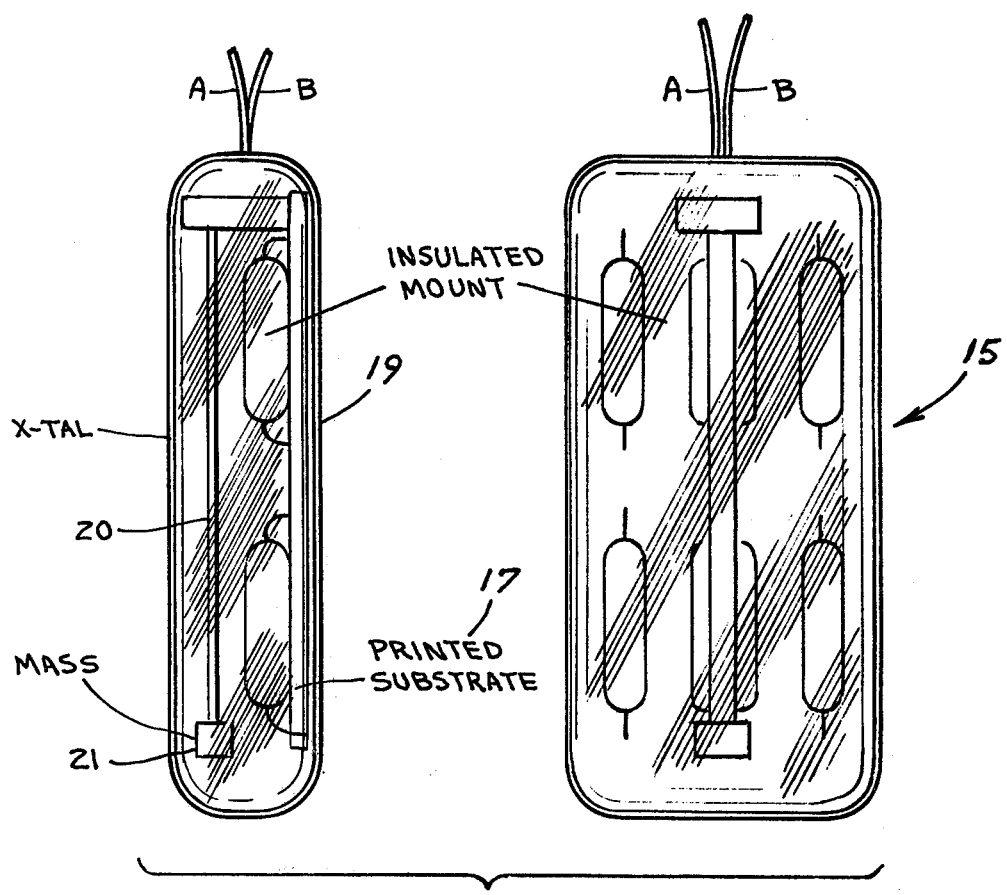
FIG. 3 is a greatly enlarged composite view in elevation and top plan of the invention herein mounted on a substrate and encapsulated, and is merely intended to show a form of an exterior view.

A prior art pacemaker 10 is shown in FIG. 2 which embodies a constant timing resistor PR1 and a capacitor PC1. Said resistor PR1 taken with said capacitor provides a constant or fixed rate pacing pulse rate. This circuitry is well known in the art as is the device generally as shown and hence will not be further described.

The device 15 will be embodied in said pacemaker 10 as will be described to substitute for the resistor PR1 and will thus provide said pacemaker with a variable pacing pulse rate as a function of physical activity.

It will be understood that said device 10 as encapsulated will be miniaturized to be of a very small size in being attached to said pacemaker to be integral therewith.

Said device 15 comprises a high impedance self voltage generating member or means 20. Shown here is a very thin elongated member projected under a cantilevered suspension having a small weighted mass 21 of a high density substance such as lead carried at its free end. Said mass will be of sufficient weight to give a desired relative movement responsive to physical activity to produce a desired voltage output as will be described. Said means 20 generally will be oriented to be disposed along its axis in a vertical plane with respect to the manner in which a pacemaker is generally implanted within a subject when the upper body portion of the subject is in an upright position. However, said means may otherwise be oriented to respond to physical movement of whatever direction. The word subject as used herein will refer to a person having an implanted cardiac pacemaker.

Thus said device 15 contained within a cardiac pacemaker will be implanted normally within the chest wall of a subject and said member 20 will be free to move as by vibration or swinging movement in response to physical movement of the subject.

The high impedance self voltage generating means or member 20 in the embodiment here presented is described as being formed of a piezo-electric material which material is of such character that an AC voltage is generated from a strain being placed by its vibration or relative movement in response to physical activity.

Hence, said voltage generated in connection with a cardiac pacemaker becomes a function of the physical activity of the subject. The voltage output of a piezo-electric material is at an extremely high impedance level, i.e., the voltage generated placed into any essentially resistive load deteriorates very rapidly.

Said piezo-electric material has a high measurable voltage output per strain input.

In the circuit with said member 20 are diodes D1 and D2 which rectify the AC voltage generated by said member 20.

The voltage generated and rectified is used to charge in the present embodiment the capacitors C1 and C2. Capacitor C1 is a capacitor chosen to have a small value and to charge very rapidly in order to give a very fast response to the physical movement of the subject to increase the pulse rate of the subject, as will be described.

The capacitor C2 is chosen to have a much larger value than said capacitor C1 and is charged over a relatively long period of time through a resistor R1 and its function is hereinafter described.

The diode D1 provides a path for positive DC voltage to both of said capacitors. Said diode D2 provides a return path for the discharge of member 20 when it has movement in a direction to generate negative voltage.

The resistor R3 in series with said capacitors forms a discharge path for said capacitor C1 and for said capacitor C2 through resistor R1.

The selection of the specific values of the capacitors and the related resistors is a matter of design to achieve the desired variation in a pacing pulse rate.

The voltage generated is applied by said capacitors to a member 25 which in the present embodiment is described as an N-channel depletion mode field effect transistor, the same being commonly known as a J-FET. Said member 25 has a gate G and a drain DR1 and a source S1 forming a drain source path DR1 - S1. For all purposes herein, said gate is completely electrically isolated from its drain and source. Said drain source path represents a resistance path. Said gate being virtually non-conductive becomes voltage controlled to create a variable resistance in the path between said drain and said source. This resistance decreases proportionally as positive voltage is applied to said gate.

In connecting or embodying said device 15 into the circuitry of said prior art pacemaker 10, the drain DR1 is connected through terminal A to the primary voltage supply 11 of said prior art pacemaker. The source S1 is connected to said prior art pacemaker to substitute for the resistor PR1 by being connected to the capacitor PC1. The resistor PR1 is thus replaced and the constant pulse rate timing thereof is replaced by the variable pulse rate timing produced by the device 15 through the drain DR1 - S1 path.

When the subject engages in movement said member 20 having relative movement responsive to the movement of the subject, it immediately generates an AC voltage of which the diode D1 permits positive voltage to charge the capacitor C1. The subject by merely taking one or two steps as up a flight of stairs would provide sufficient physical activity to actuate said member 20 to charge the capacitor C1. The capacitor C1 having been chosen to have a small value charges very rapidly and in effect immediately places a positive potential upon the gate G.

As described, the gate G is controlled by the voltage applied to it and in response thereto reduces the resistance in the drain-source path DR1 - S1 to increase the conduction of current through said path and thus there is an increase in the pacing pulse rate of the pacemaker 10.

When the subject ceases physical movement the capacitor C1 will discharge rapidly and apply no further voltage to said gate G. The capacitor C2 through the resistor R1 will discharge less rapidly and will continue to apply voltage to gate G and this voltage will diminish as the capacitor becomes gradually discharged and this in turn is proportional to the length of time of the physical activity of the subject, or in other words, proportional to the length of time that capacitor C2 has been charging. Thus the resistance in the DR1 - C1 path will gradually increase and the conduction of current through this path will accordingly decrease as will the rate of the pacing pulse.

The result here is that the increased rate of the pacing pulse rate will fall back or return to the basal or rest rate gradually over a period of time and this precludes a sudden rate shift of the pulse from that in connection with heavy exertion to that of a rest state.

The precise rest rate of the pacing pulse is a matter of design of the components described making up the device 15.

The time constant for the discharge of said capacitors is determined by said capacitor C1 and by said capacitor C2 taken with its resistor R1 in connection with a resistor R3 in series therewith, said resistor R3 forming the discharge path for said capacitors.

Thus, where the pacemaker 10 would otherwise have a fixed or constant rate of a pacing pulse, the substitution of applicant's device for the resistor PR1 and taken in connection with the capacitor PC1 causes the prior art pacemaker to have a variable pacing pulse rate, one which approaches the character of a normal pulse rate.

The current path of the pacemaker 10 is from its primary voltage supply 11 through the path DR1 - S1 to the capacitor PC1. As described, resistance to the conduction of current through the path DR1 - C1 is varied as controlled by the gate G and in turn this control is proportional to the physical activity of the subject.

In view of the above description of the pacing pulse rate being a function of physical activity of the subject, in the absence of physical activity, there may be set a lower rate than would be present in the absence of a variable timing of this rate. Thus basic pulse rate in a rest or non-active state may be set as on the order of 67 instead of on the order of 72 beats per minute which would be the case in a constant or fixed rate prior art pacemaker. The lower rate would be a more comfortable rate for the subject in the absence of activity and in view of which the subject would expend less body sugar, his metabolism rate would be lower and the subject would have a more restful sleep at a lower pulse rate. Further, the lower basic pulse rate reduces the requirement for drawing on the battery life.

The device 20 is completely fail safe in its arrangement. The resistor R4 establishes a low rate limit in the subjects complete rest state wherein for all practical purposes, the path DR1 - S1 is an open circuit. In addition the resistors R5 and R6 are in series with said drain source path DR1 - S1.

If by some condition the member 25 were to completely open due to a component failure, it would be by-passed by said resistors R4, R5 and R6 in series with said capacitor PC1 whereby there will be maintained a predetermined basic pulse rate as established by the time constants of said resistors taken with said capacitor. On the other hand, if said member 25 were to short out, said resistors in series with said capacitor PC1 would not permit the basic pulse rate to exceed a given predetermined basic pulse rate.

In a prior art pacemaker, as the primary voltage battery diminishes over a period of time, there is a corresponding decrease in the basic pulse rate. This would adversely effect the subject who would become aware of the decrease in the rate of his heart beat. This is based on the assumption that persons having a pacemaker implanted are going to be rather hypertensive just by virtue of the fact of the implant of the pacemaker and sensing that a battery is commencing to fail and that the heart beat is slowing up.

With respect to the device herein, as the primary battery life diminishes over a period of time, the voltage drop across the resistor R6 becomes smaller and the source S1 of the member 25 becomes more negative, the gate G consequently becomes more positive and allows for a greater degree of conduction through the DR1 - S1 path. In other words, there is a smaller resistance whereby the pacing pulse rate will increase very slowly as a function of diminishing voltage supply.

With a basic pacing pulse rate increasing such as from 67 to 72 beats per minute with a depletion of battery voltage, this will indicate to the subject the need for inspection of the primary source of voltage, or in other words, inspection of the battery. In the meantime, the subject is heartened by the fact that his heart beat is not decreasing but is maintaining a slightly higher than normal rate.

Thus the device described herein for the purpose of modifying a prior art pacemaker by becoming an integral part thereof provides the advantages of having a pacemaker with an otherwise fixed pulsing rate to have a pulsing pace rate variable as a function of physical activity. It provides an improved indication of the need for battery inspection or change and to conserve primary battery life by diminishing the demand for battery power during quiet or rest periods but more important than any of these is the fact that it provides for a lower pulsing rate during quiescent or rest times because of the fact that the physical activity of the subject varies a pulsing rate to what is required by the amount of exertion involved in the physical activity. Thus the pacemaker adapts itself to the specific needs of the subject.

It will of course be understood that various changes may be made in form, details, arrangement and proportions of the parts without departing from the scope of the invention herein which, generally stated, consists in an apparatus capable of carrying out the objects above set forth, in the parts and combinations of parts disclosed and defined in the appended claims.

What is claimed is:

1. In combination with a cardiac pacemaker having a primary power supply and primary circuit including a constant timing resistor and a capacitor forming means establishing a fixed rate pacing pulse, a variable timing device making said fixed rate variable as a function of the physical activity of the subject wearing the pacemaker comprising a circuit including
   a high impedance AC voltage generating means self-generating voltage as a function of the physical activity of said subject,
   means rectifying said voltage producing a direct current,
   a first rapidly charging capacitor,
   a second capacitor having a resistor in series therewith charging proportionally to the term of physical activity of said subject,
   discharge means in circuit with said first mentioned capacitor and with said second mentioned capacitor and said resistor,
   said voltage generating means charging said capacitors,
   a field effect transistor having a gate having a high input impedance, and having a drain and a source forming a drain-source current resistance path, said gate responding to voltage applied thereto varying the resistance of said drain-source path,
   said drain-source path replacing said fixed rate constant timing resistor in said circuit of said pacemaker and substituting a variable rate as a function of its resistance,
   said first mentioned capacitor applying voltage to said gate directly responsive to the physical activity of said subject, said gate responsive to the voltage applied thereto reducing the resistance of said drain-source path to increase conduction therethrough and increase the pacing pulse rate of said pacemaker as a function of the physical activity of said subject, and
   said second capacitor through said resistor in series therewith applying voltage to said gate upon cessation of physical activity of said subject, said voltage being applied proportionally to the term of physical activity of said subject as said capacitor discharges, thus reducing the voltage applied to said gate with resulting increase in resistance in said drain source path and a consequent decrease in said pacing pulse rate corresponding to the decrease which would take place within a normal pulse rate after a period of physical activity.

2. The structure set forth in claim 1, wherein said voltage generating means comprises a piezo-electrical circuit.

3. The structure set forth in claim 1, wherein
   said first capacitor and said second capacitor with the resistance in series therewith and said discharge means comprise a time constant making the fixed rate of the said pacemaker increase and decrease in rate as a function of the physical activity of the subject wearing the pacemaker.

4. The structure set forth in claim 3, wherein
   said discharge means comprises a resistor chosen to establish the lower limit of said pacing pulse rate.

5. The structure set forth in claim 3, wherein
   said discharge means comprises a resistor chosen to establish the lower limit of said pacing pulse rate in the event of said drain-source path becoming virtually an open circuit.

6. The structure set forth in claim 3, including
   resistors in series with said drain-source path establishing the upper limit of said pacing pulse rate independently of the operation of said circuit.

7. The structure set forth in claim 1, wherein
   said drain source path is in circuit with the primary voltage supply of said pacemaker, and
   said drain source path substitutes for the charging resistance of said pacemaker.

8. The structure set forth in claim 7, including
   a pair of resistors in series with said drain-source path establishing an upper limit rate for said pacing pulse rate.

9. The structure set forth in claim 1, wherein
   said second capacitor in series with its resistor are chosen to charge incrementally over the period of time of the physical activity of said subject wearing said pacemaker.

10. The structure set forth in claim 1, including
    a resistor acting as a source follower for said source of said transistor,
    said resistor having the voltage drop thereacross decrease responsive to a voltage drop in the primary power source of said pacemaker, said source becoming more negative responsive to said voltage drop and said gate becoming more positive responsive to said source becoming more negative, whereby said resistance in the drain source path of said transistor decreases and the pacing rate of said pacemaker increases as a function of a decrease in the primary power supply.

11. In combination with a cardiac pacemaker having a primary voltage circuit including a constant timing resistor and a capacitor forming means establishing a fixed rate pacing pulse, a variable timing device making said fixed rate variable as a function of the physical activity of the subject wearing the pacemaker comprising a circuit including means generating a high impedance AC voltage as a function of the physical activity of the subject wearing said pacemaker, means charged by said voltage generating means, a field effect transistor having a high impedance input gate and a drain and a source forming a drain-source resistance path replacing said fixed rate constant timing resistor in the primary voltage circuit of said pacemaker, said drain being connected to the primary voltage source of said pacemaker and said source substituting for the constant timing resistor of said pacemaker, and said means charged by said voltage generating means applying voltage directly to said gate during the term of physical activity, said applied voltage being proportional to said physical activity and applying said voltage at a decreasing rate responsive to a decrease in physical activity whereby the passing pulse rate is comparable to a normal heart action.

12. The structure set forth in claim 11, wherein
said second means comprises
a rapidly charging capacitor,
a capacitor in circuit with a resistor charging over the period of time of physical activity of the subject, and
a resistor forming the discharge path for said capacitors to said gate.

* * * * *